United States Patent
Grohman et al.

(10) Patent No.: US 6,558,660 B2
(45) Date of Patent: *May 6, 2003

(54) METHOD FOR REGULATING IL-10 WITH IL-9, AND APPLICATIONS THEREOF

(75) Inventors: Ursula Grohman, Perugia (IT); Jacques Van Snick, Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/898,627

(22) Filed: Jul. 2, 2001

(65) Prior Publication Data

US 2002/0136703 A1 Sep. 26, 2002

Related U.S. Application Data

(62) Division of application No. 09/490,825, filed on Jan. 25, 2000, now Pat. No. 6,328,955.

(51) Int. Cl.[7] .......................... A61K 38/20; A61K 38/19
(52) U.S. Cl. .......................... 424/85.2; 424/85.1; 514/2; 514/12; 514/263; 514/885
(58) Field of Search ................ 424/85.2, 85.1; 514/2.12, 263, 885

(56) References Cited

PUBLICATIONS

Gerard, et al., "Interleukkin 10 Reduces the Release of Tumor Necrosis Factor and Prevents Lethality In Experimental Endotoxemia" J. Exp. Med. 177:547–550 (1993).

Howard, et al, "Interleukin 10 Protects Mice from Lethal Endotoxemia" J. Exp. Med. 177: 1205–1208 (1993).

Marchant, et el, "Interleukin 10 Controls Interferon–γ and Tumor Necrosis Factor Production During Experimental Endotoxemia" J. Immunol 24:1167–1171 (1994).

Houssiau, et al., "A Cascade of Cytokines Is Responsible for IL–9 Expression in Human T Cells" J. Immunol 154:2624–2630 (1995).

Grencis, et al, "Host Protective Immunity to *Trichinella spiralis* in mice: activation of Th cell subsets and lymphokine secretion in mice expressing different response phenotypes", Immunology 74:329–332 (1991).

Primary Examiner—Gary Kunz
Assistant Examiner—Fozia Hamud
(74) Attorney, Agent, or Firm—Fulbright & Jaworski LLP

(57) ABSTRACT

The invention involves the recognition of IL-9 as a molecule involved in induction of IL-10. Administration of IL-9 leads to protection against conditions where IL-10 production is warranted, such as infections by Gram negative bacteria. Examples of such conditions are septic shock and endotoxemia. Also a part of the invention are methods of treatment where IL-9 and a phosphodiesterase inhibitor are administered to a subject. Compositions, such as kits which include these two components are a part of the invention, as is treatment of conditions involving excess IL-10 production by administering an IL-9 inhibitor.

6 Claims, 5 Drawing Sheets

SEQUENCE LISTING

```
<160> NUMBER OF SEQ ID NOS: 2

<210> SEQ ID NO 1
<211> LENGTH: 30
<212> TYPE: DNA
<213> ORGANISM: Mus musculus
<220> FEATURE:
```

-continued

```
<400> SEQUENCE: 1
tccttaatgc aggactttaa gggttacttg                                    30

<210> SEQ ID NO 2
<211> LENGTH: 30
<212> TYPE: DNA
<213> ORGANISM: Mus musculus
<220> FEATURE:

<400> SEQUENCE: 2
gacaccttgg tcttggagct tattaaaatc                                    30
```

METHOD FOR REGULATING IL-10 WITH IL-9, AND APPLICATIONS THEREOF

RELATED APPLICATION

This application is a divisional of application Ser. No. 09/490,825, filed Jan. 25, 2000 now U.S. Pat. No. 6,328,955.

FIELD OF THE INVENTION

The invention relates to the induction of interleukin-10 ("IL-10") by interleukin-9 ("IL-9"). This unexpected effect leads to an ability to use IL-9 in prophylaxis and treatment of conditions such as septic shock and endotoxemia.

BACKGROUND AND PRIOR ART

Interleukin-9 ("IL-9" hereafter) is a pleiotropic cytokine, produced primarily by T helper cells. It was originally described as a growth factor for T cells, and then for mucosal type mast cells. Additional properties have been ascribed to this cytokine, including, but not being limited to, erythroid differentiation, Ig production, neuronal differentiation, granzyme expression, and induction of expression of high affinity IgE receptors in T helper clones. Review articles discussing these and other properties are Renauld, et al, Adv. Immunol. 54: 79 (1993); and Demoulin, et al, Int. Rev. Immunol. 16:345 (1998), both of which are incorporated by reference. The molecule was first observed in murine form, and was referred to as P40. The molecule was isolated and cloned, as was its receptor, in both murine and human form. See, e.g., U.S. Pat. Nos. 5,208,218; 5,157,112; 5,580,753; 5,587,302; 5,734,037; 5,750,377; 5,116,951; 5,180,678; and 5,789,237, all of which are incorporated by reference. IL-9 has been implicated in inhibiting production of IgE and enhancing production of IgG (U.S. Pat. Nos. 5,132,109 and 5,246,701); in modulating cell apoptosis (U.S. Pat. No. 5,824,551), treatment of autoimmune disorders (U.S. Pat. No. 5,830,454), and in treatment of interstitial lung disease (U.S. Pat. No. 5,935,929). All of these patents are incorporated by reference.

In view of its restricted production by Th2 clones in vitro (Gessner, et al, Immunobiology 189:419 (1993) as well as its expression in Th2 type responses in vivo (Grencis, et al, Immunology 74:329 (1991); Svetic, et al, J. Immunol. 150:3434 (1993); Faulkner, et al, Infect. Immunol. 66:3832 (1998)), IL-9 is considered to be a Th2 cytokine that is inducible by both IL-4 dependent and IL-4 independent pathways. See Gessner, et al, supra; Kopf, et al, Nature 362:245 (1993); Monteyne, et al, J. Immunol. 159:2616 (1997). Others have described dependence of IL-10 on IL-9 (Grencis, et al, supra; Houssiau, et al, J. Immunol. 154:2624 (1995)). Further, IL-9 has been implicated in response to parasitic infections (Grencis, et al, supra; Svetic, et al, supra; Faulkner, et al, supra; Else, et al, Immunology 75:232 (1993)); allergies (Petit-Frere, et al, Immunology 79:146 (1993)); and inflammatory processes (Louahed, et al, J. Immunol. 154:5061 (1995)); however, the role of interleukin-9 in antibacterial host defense has not been investigated.

Septic shock is a condition resulting from uncontrolled, sequential release of mediators having proinflammatory activity following infection with Gram negative bacteria, and in response to endotoxins. See, e.g., Tracey, et al, Science 234:470 (1986); Alexander, et al, J. Exp. Med. 173:1029 (1991); Doherty, et al, J. Immunol. 149:1666 (1992); Wysocka, et al, Eur. J. Immunol. 25:672 (1995). Endotoxin exerts its effect by inducing potent, macrophage activation, and release of cytokines such as TNF-α, IL-1, IL-6, IL-12, and IFN-γ. See Van Deuren, et al, J. Pathol. 168:349 (1992). In particular, IL-12, in concert with TNF-α, or B7 costimulation, can act as a potent inducer of IFN-Γ production by T and NK cells. See D'Andrea, et al., J. Exp. Med. 178:1041 (1993); Murphy, et al, J. Exp. Med. 180:223 (1994); Kubin, et al, J. Exp. Med. 180:211 (1994). The central role of proinflammatory cytokines in the pathogenesis of endotoxic shock is underlined by the occurrence of high levels of circulating cytokines in both humans and experimental animals during endotoxemia. See Stevens, et al, Curr. Opin. Infect. Dis. 6:374 (1993).

The triggering of regulatory mechanisms during sepsis can oppose macrophage activation. (Heumann, et al, Curr. Opin. Infect. Dis. 11:279 (1998)). This, in turn, can alleviate an overwhelming, dysregulated inflammatory response, which leads to pathological effects, and potential death by the host. A substantial body of literature shows that anti-cytokine action can improve the outcome of subjects challenged by LPS or Gram negative bacteria. Beutler, et al, Science 229:689 (1985), and Heinzel, et al, J. Immunol. 145:2920 (1990), teach administration of neutralizing anti-cytokine antibodies, while Ohlsson, et al, Nature 348:550 (1990), teach administration of IL-1R antagonists, Bozza, et al, J. Exp. Med. 189:341 (1999) teach targeting of genes encoding proinflammatory cytokines, and both Pfeffer, et al, Cell 73:457 (1993), and Car, et al, J. Exp. Med. 179:1437 (1994), teach that administration of cytokine receptors can diminish lethality in experimental endotoxemia.

Both interleukin-10 ("IL-10"), and interleukin-4 ("IL-4") have been shown to be efficacious in treatment of septic shock and LPS induced pathology. With respect to IL- 10, see Marchant, et al, Eur. J. Immunol. 24:1167 (1994); Howard, et al, J. Exp. Med. 177:1205 (1993); Gerard, et al, J. Exp. Med. 177:547 (1993). With respect to IL-4, see Baumhofer, et al, Eur. J. Immunol. 28:610 (1998), Jain-Vora, et al, Infect. Immun. 66:4229 (1998), and Giampetri, et al Cytokine 12(4): 417–421 (2000).

The known efficacy of IL-4 and IL-10, however, does not permit the skilled artisan to predict efficacy of IL-9 in treating and preventing septic shock and/or endotoxemia. The known properties of IL-9 are not such that one could attribute efficacy against Gram negative bacteria.

It has now been found that IL-9 actually induces IL-10, leading to efficacy in preventing septic shock and endotoxemia. This is contrary to expectation, since it has in fact been argued that IL-10, in conjunction with IL-4, stimulates IL-9 production by human PBLs, and that IL-9 production is, in fact, inhibited by antibodies to IL-10. See Houssiau, et al, J. Immunol. 154:2624 (1995). Hence, it is quite surprising and unexpected that IL-9 induces IL-10, and can be used in methods to prevent and/or to treat conditions where an increase in IL-10 levels is desirable. These, inter alia, are features of the invention, as elaborated in the examples and disclosure which follow.

BRIEF DESCRIPTION OF THE FIGURES

FIGS. 3A, 3C & 3E resulted from *P. aeruginosa* treated mice, while FIGS. 3B, 3D & 3F represent data from LPS challenge.

DETAILED DESCRIPTION OF PREFERRED EMBODIMENTS

EXAMPLE 1

Giampetri, et al, Cytokine 12(4): 417–421, the disclosure of which is incorporated by reference, describe an animal model which is useful in determining protective efficacy of a test substance in a live sepsis model. This model was used in these experiments. To elaborate, hybrid mice (BALB/c CrxDBA/2Cr) $F_1$ (CD2 $F_1$) of both sexes, ranging in age from 2–4 months were used. Mice were injected, intravenously, with $10^{10}$ cells of *P. aeruginosa* (serotype 10), as described by, e.g., Campanile, et al, Cell. Immunol. 128:250 (1990); Campanile, et al, Cell. Immunol. 147:341 (1993); Campanile, et al, Eur. J. Pharmacol. 307:191 (1996). The microorganism was cultured in tryptic soy broth using standard conditions, and incubated at 37° C. for 18–24 hours under constant aeration. After the overnight culturing, the microorganisms were centrifuged, forming a soft pellet which was then resuspended in phosphate buffered saline. The dose of microorganisms referred to supra was then administered. This inoculum size is known to be lethal in more than 90% of test animal populations.

Prior to administration of the *P. aeruginosa*, animals were treated with either IL-4 (3 $\mu$g/mouse), together with 30 $\mu$g of anti-IL-4 monoclonal antibodies, (this composition has been shown to improve bioavailability of IL-4, and to provide 100% protection against fatal sepsis, (see Giampetri, et al, supra), recombinant murine IL-9 produced in a baculovirus model in accordance with Druez, et al, J. Immunol. 145:2494 (1990), incorporated by reference (varying doses, administered 1 or 24 hours, or at both 1 and 24 hours prior to challenge), IL-9 heat inactivated by autoclaving, or phosphate buffered saline. The interleukins and PBS were all administered intraperitoneally. Pentoxifylline was also administered intraperitoneally.

Figure 1:
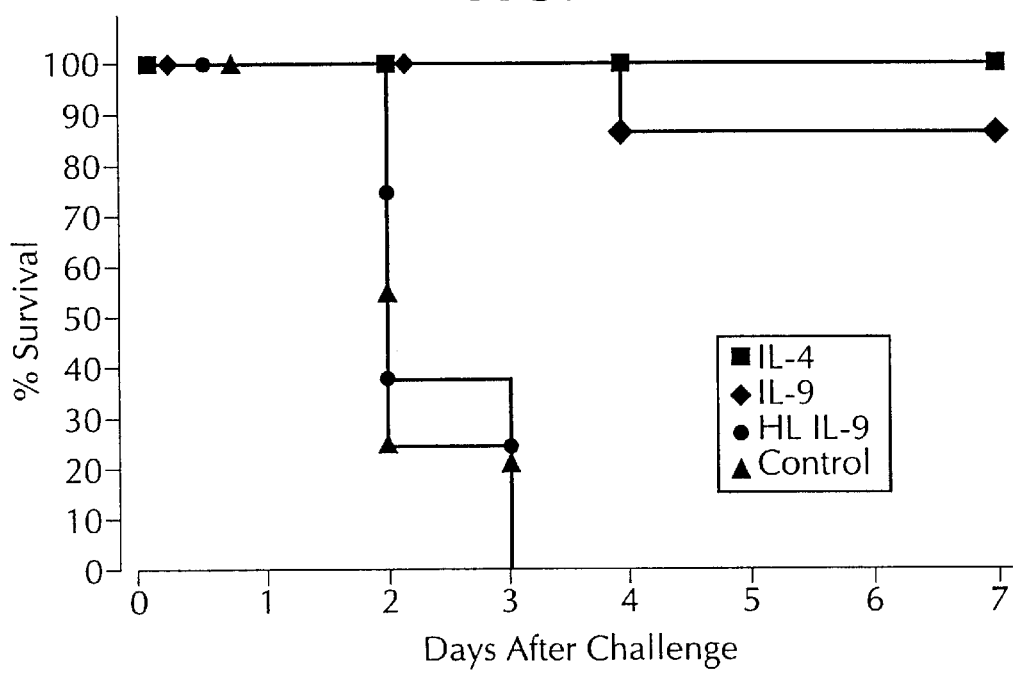
FIG. 1 shows percentage survival of experimental animals which received interleukin-4 ("IL-4"), interleukin-9 ("IL-9") heat inactivated IL-9 ("HI-IL-9"), or a control, prior to challenge with P. aeruginosa.

The results of these experiments are presented in FIG. 1. "H" is an abbreviation for "heat inactivated." When the data from several independent experiments were pooled and analyzed, it was seen that IL-9 reproducibly and significantly protected the subject animals against onset of lethal septic shock. The survival rate was about 80%.

EXAMPLE 2

Figure 2:
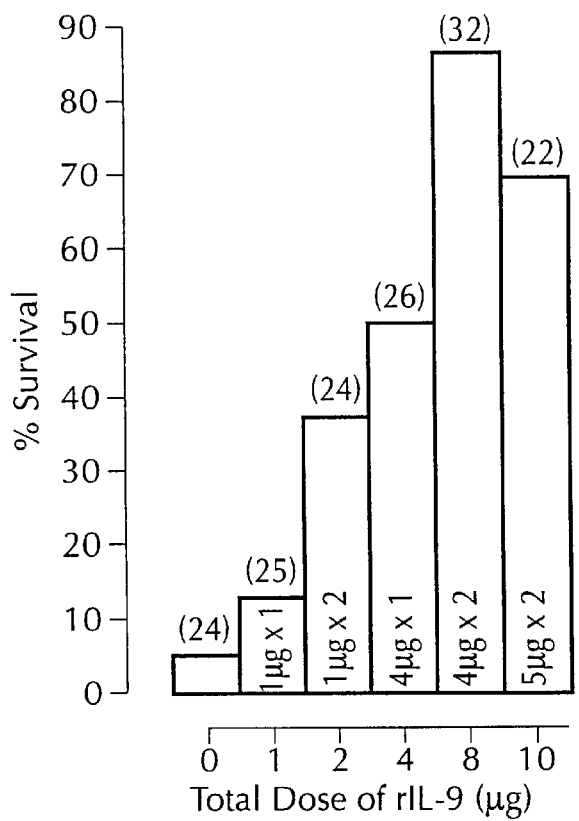
FIG. 2 summarizes data showing the effect of different IL-9 doses on mice infected with P. aeruginosa.

The experiments described supra were repeated, using a variety of doses, and both prophylactic and post-challenge administration. The results, set forth in FIG. 2, depict data obtained using 1 or 5 $\mu$g of IL-9, administered 24 hours before, or 24 hours and 1 hour before bacterial challenge. It is noteworthy that a single 4 $\mu$g dose of IL-9 24 hours before bacterial challenge was associated with a 50% cure rate, even without a second dose. A single treatment of 4 $\mu$g near the time of infection, and as much as 3 hours post challenge, provided marginal benefit.

EXAMPLE 3

It has been observed, previously, that there is a strong association between development of fatal septic shock and production of TNF-$\alpha$. See, e.g., the Campanile papers, cited supra. In addition, IL-12 and IFN-$\gamma$ are pro-inflammatory cytokines thought to have a pathogenetic role in both septic shock and endotoxemia. See D'Andrea, et al, J. Exp. Med. 178:1041 (1993). Murphy, et al, J. Exp. Med. 180:223 (1994); Kubin, et al, J. Exp. Med. 180:211 (1994). In view of the results secured in examples 1 & 2, studies were undertaken to measure serum levels of TNF-$\alpha$, IL-12 p40, and IFN-$\gamma$, in subject animals challenged with *P. aeruginosa* in the manner described supra, or lipopolysaccharide antigen ("LPS" hereafter), that were also treated with IL-9.

Figure 3:
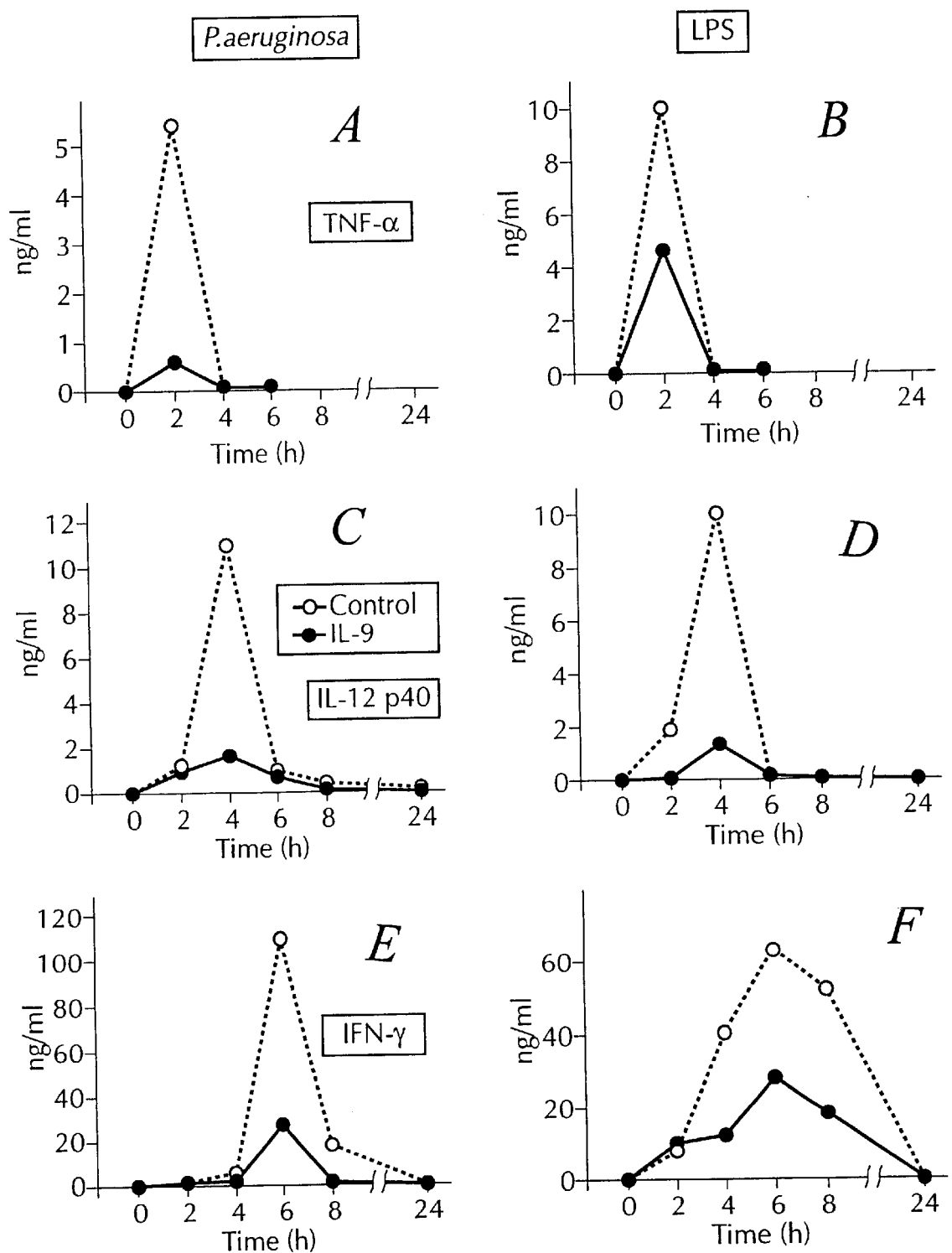
FIG. 3(A–F) depict, respectively, serum levels of TNF-, IL-12 p40 and IFN-Y of mice that had been challenged with P. aeruginosa or lipopolysaccharide antigen ("LPS"), and had been treated with IL-9.

In these experiments, mice were injected, intraperitoneally, with 850 $\mu$g of LPS, which had been determined previously to constitute an $LD_{90}$. All animals received doses of IL-9 as described supra, 24 and 1 hour prior to challenge. Sera were analyzed 2, 4, 6, 8, and 24 hours following challenge, using either a standard bioassay for TNF-$\alpha$ (cytotoxicity to TNF-$\alpha$ sensitive WEH1 164 cells), or via an immunoassay (IL-12p40 and IFN-$\gamma$). FIG. 3 presents these results, in terms of mean values for individual mice. It will be seen that the IL-9 exerted a dramatic, early effect on expression of the cytokines, with drastic reduction in all three cytokines at 2, 4 and 6 hours. The TNF-$\alpha$ levels were most drastically reduced, showing a 10-fold drop in *P. aeruginosa* treated mice, and better than a twofold drop in LPS challenged animals. Notwithstanding the drop, the high, baseline expression of circulating TNF-$\alpha$ in mice challenged with LPS led to death in the majority of the animals tested.

EXAMPLE 4

It has been shown, by Stevens, et al, Curr. Opin. Infect. Dis. 6:374 (1993), that phosphodiesterase inhibitors modulate the production of TNF-$\alpha$ and improve the outcome of animals afflicted with experimental sepsis. Pentoxifylline is one such inhibitor that confers protection. This has led to the hypothesis that TNF-$\alpha$ overproduction is involved and is important, in the live sepsis model described herein. See Campanile, et al, Eur. J. Pharmacol. 307:191 (1996). These observations suggested the experiments described herein, which were designed to determine if the post-challenge therapeutic effect of IL-9 could be amplified if administered with a phosphodiesterase inhibitor.

Figure 4:
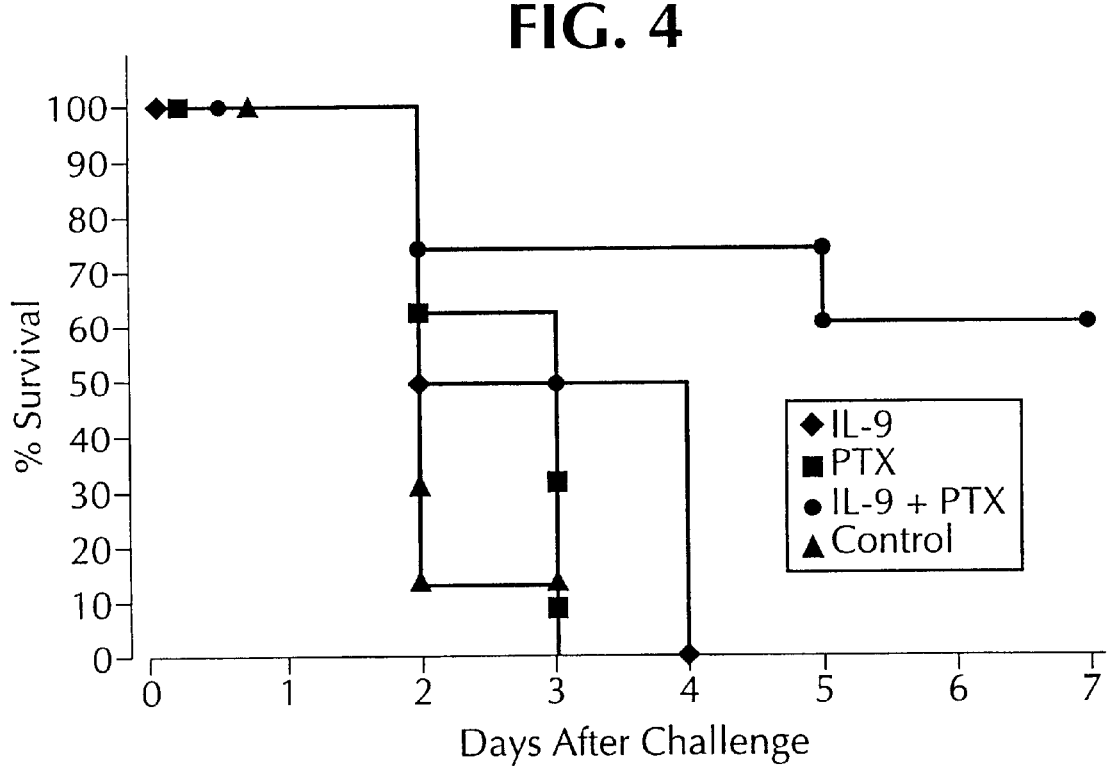
FIG. 4 shows the results of survival studies when mice were treated with pentoxifylline and IL-9.

To test this, mice received pentoxifylline at a dose of 30 mg/kg of body weight 1 hour before challenge with bacteria. The animals received a dose of murine IL-9 (4 $\mu$g) three hours post infection. The results, presented in FIG. 4, compare treatment with the phosphodiesterase inhibitor alone, IL-9 alone, a control, and the combination therapy. Combined treatment resulted in survival of most of the animals, thus suggesting the use of IL-9 in combination with phosphodiesterase inhibitors for treatment of septic shock/endotoxemia.

EXAMPLE 5

The results obtained in example 4, spra, suggested that TNF-$\alpha$ overproduction is not the only mechanism involved. In view of the observations of Giampetri, et al, supra, serum levels of the anti-inflammatory cytokines IL-4 and IL-10 were measured in the sera of mice that had been challenged, either with the whole bacteria or with LPS, as described supra, and had received IL-9 24 and 1 hour prior to challenge, as described supra. Levels were measured via ELISAs, 2, 4, 6, 8, and 24 hours after challenge.

Figure 5:
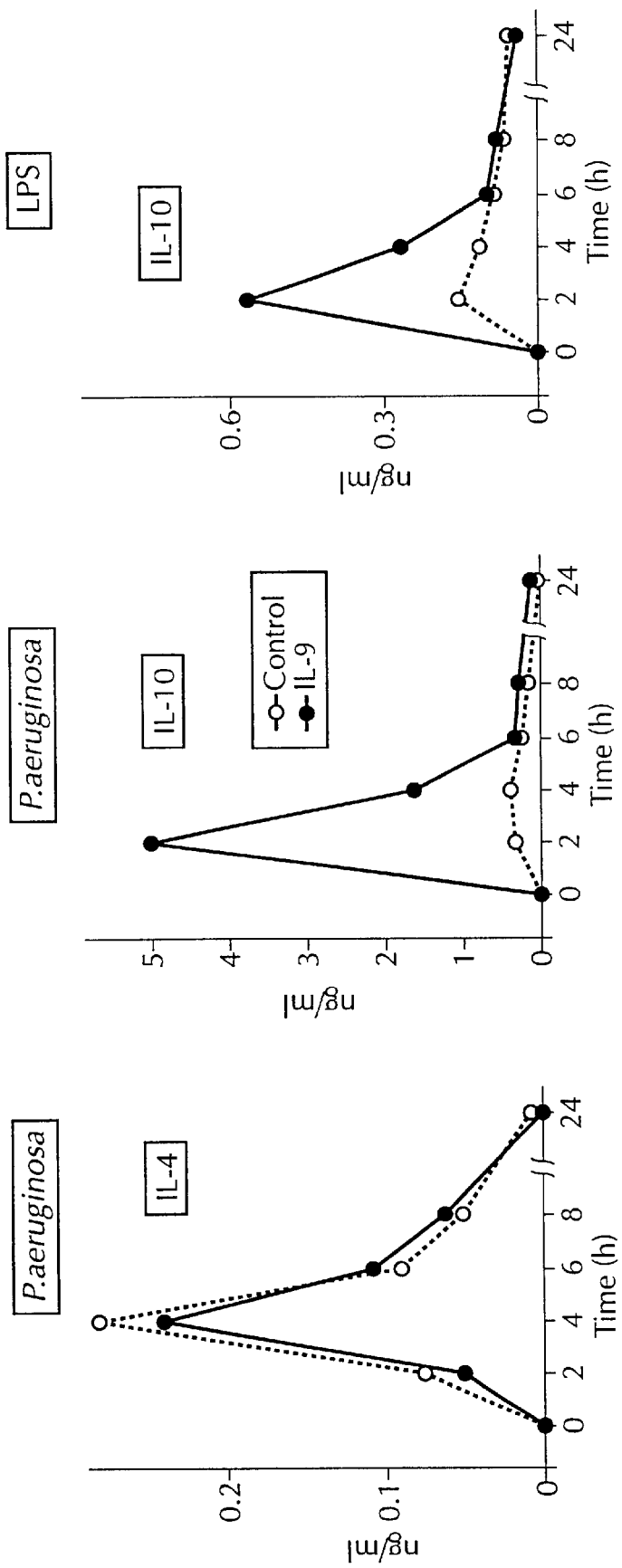
FIG. 5 presents data showing circulating levels of IL-4 and IL-10 in mice that had been challenged with either *P. aeruginosa* or LPS and treated with IL-9.
Figure 6:
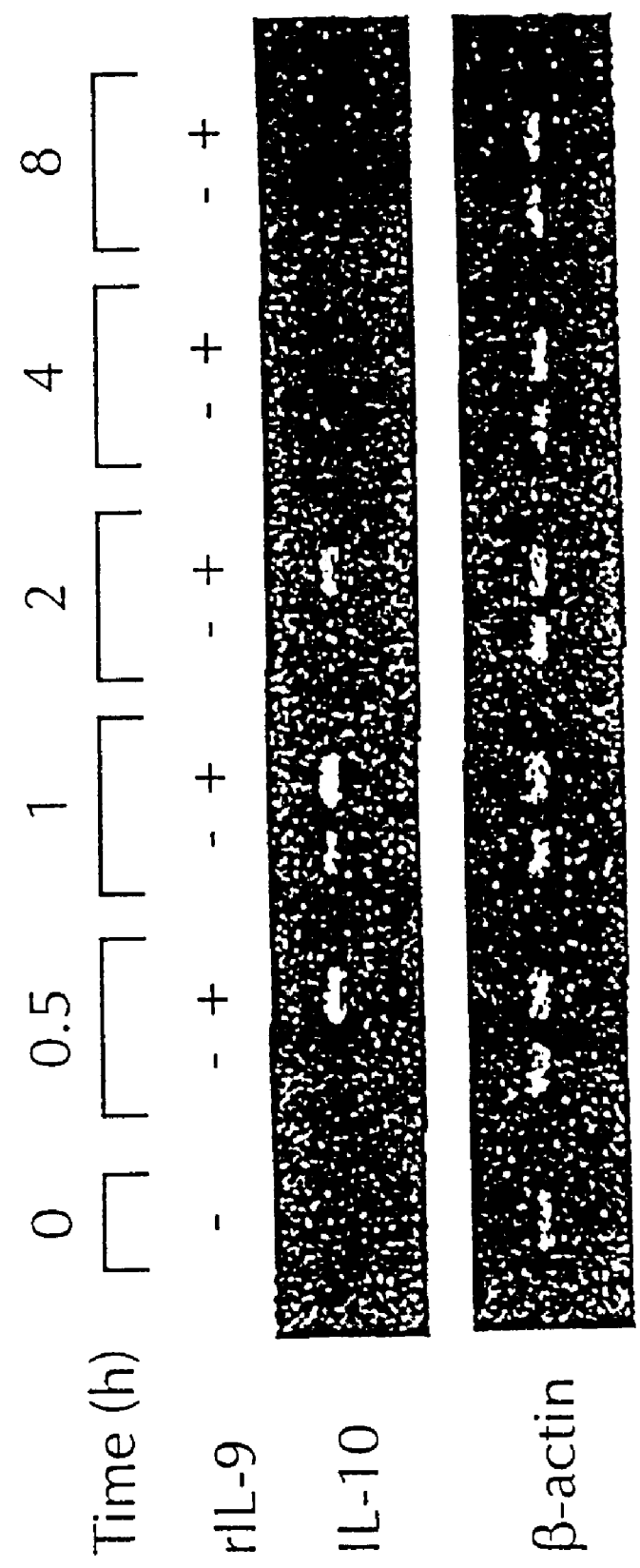
FIG. 6 sets forth data on DNA expression of IL-4 and IL-10 following treatment with IL-9.

IL-4 production was limited, and peaked at 4 hours post infection. The administration of IL-9 did not appear to have any effect on it. On the other hand, the amount by which IL-10 levels increased at 2 hours following Pseudominas infection was striking. The same effect, albeit a lesser one, was seen in the LPS challenged mice. Results are summarized in FIG. 5.

EXAMPLE 6

The experiments described herein report analyses of expression of IL-10. Specifically, total RNA was isolated from spleen cells of challenged mice at different points in time (0.5, 1, 2, 4, and 8 hours). Isolation was carried out in accordance with Campanile, et al, Eur. J. Pharmacol. 307:191 (1996), and Houssiau, et al, J. Immunol. 154:2624 (1995), incorporated by reference. These references also describe the PCR protocols used for amplifying transcripts of β-actin (control), and IL-10. Commercially available primers were used to amplify β actin, and the 5' and 3' primers for IL-10 were, respectively:

```
tccttaatgc aggactttaa gggttacttg  (SEQ ID NO:1)
``` and

```
gacaccttgg tcttggagct tattaaaatc  (SEQ ID NO:2).
```

The amplification product for β actin should be 540 base pairs in length, and that of IL-10, 256 base pairs. Products were analyzed via 1.5% agarose gel electrophoresis, and visualized by ethidium bromide staining. Transcripts specific for IL-10 were hardly detectable in the spleens of control mice, but there was extensive expression after infection in animals which had received IL-9.

The foregoing examples set forth the features of the invention, which include a method for inducing interleukin-10 production by administration of an amount of interleukin-9 sufficient to induce interleukin-10 production. This can be done either in vitro, or more preferably in vivo. The references cited supra indicate that IL-9 has been accepted as a therapeutic agent.

"Interleukin-9" or "IL-9" as used herein, mean any and all forms of these molecules. The references cited supra show that both glycosylated and non-glycosylated forms are known, as are wild type and recombinant molecules. All species of IL-9, including all mammalian and human forms are included in the definition of IL-9. Also included are truncated forms of the molecule, as long as the molecule is of a sufficient size to induce IL-10 production.

Various conditions are known where induction of IL-10 is a desired end. Exemplary of these conditions are infections by Gram negative bacteria, such as *P. aeruginosa, E. coli,* and so forth. As was shown, supra, administration of IL-9 leads to a prophylactic effect in subjects. Hence, it is advantageous to administer IL-9 to a subject at risk for developing a Gram negative bacterial infection, septic shock, or endotoxemia. Patients about to undergo surgery constitute one class of such individuals. The art will recognize other such individuals as well.

It has also been shown, supra, that IL-9, in combination with a phosphodiesterase inhibitor, can be used therapeutically to treat subjects with conditions in need of IL-10 induction, such as patients suffering from a Gram negative bacterial infection, septic shock, endotoxemia, and so forth. Exemplary of such compounds is pentoxifylline. This inhibitor is known to interact with phosphodiesterase isoform III, but other such inhibitors are known. Members of the methyl xanthine family are exemplary of these inhibitors. Such molecules are known inhibitors of TNF-α, as demonstrated by U.S. Pat. Nos. 6,015,578; 6,015,558; 6,011,067; and 6,001,828, which are incorporated by reference.

Also a part of the invention is the inhibition of IL-10 production, as it will be clear to the artisan that, in conditions where excess IL-10 production is indicated, administration of an IL-9 antagonist, such as an IL-9 specific antibody, preferably a neutralizing antibody, or a portion thereof sufficient to inhibit and/or neutralize IL-9 is administered. Humanized antibodies, monoclonal antibodies, and fragments of IL-9 specific antibodies which inhibit and/or neutralize IL-9 are exemplary of such agents.

Also a part of the invention are therapeutically useful compositions, such as kits which include a separate portion of each of interleukin-9, as defined supra, and a phosphodiesterase inhibitor, also as described supra, so that the user can administer preferred doses to a subject at an appropriate time.

With respect to dosages, the particular regime developed will vary, based upon the subject and the envisioned condition or risk. Preferably, the IL-9 is administered from 4 to 24 hours prior to anticipated need for IL-10 induction, more preferably once about 24 hours prior to the anticipated need, and a second time, around 3–6 hours, preferably about 4 hours before anticipated need. The dose administered will vary, depending upon the subject. Generally, however, a dose of from about 0.1 mg/kg to about 1.0 mg/kg of body weight, more preferably from about 0.1 mg/kg to about 0.5 mg/kg of body weight, and most preferably, about 0.2 mg/kg of body weight, per dose, is the contemplated regime.

Other aspects of the invention will be clear to the skilled artisan and need not be set forth here.

Having described preferred embodiments of the invention with reference to the detailed description, supra, it is to be understood that the invention is not limited to these precise embodiments, and that various changes and modifications may be effected by one of ordinary skill in the art without departing from the scope or spirit of the invention as defined by, e.g., the claims which follow.

We claim:

1. A method for inducing production of interleukin -10 (IL-10) in a subject in need of increased production of IL-10 comprising administering to said subject in need of increased production of IL-10 an amount of interleukin -9 (IL-9) sufficient to induce production of IL-10 in said subject.

2. The method of claim 1, wherein said subject is at risk for infection by Gram negative bacteria.

3. The method of claim 2, wherein said Gram negative bacteria are *E. coli* or *P. aeruginosa*.

4. The method of claim 1, wherein said IL-9 is human IL-9.

5. The method of claim 3, wherein said human IL-9 is recombinant human IL-9.

6. The method of claim 1, comprising administering said IL-9 intraperitoneally.

* * * * *